United States Patent
Podschun

(10) Patent No.: US 10,905,877 B2
(45) Date of Patent: Feb. 2, 2021

(54) SYSTEM AND METHOD FOR THE REGENERATION OF AT LEAST ONE SEVERED NERVE CONDUIT

(71) Applicants: Trutz Podschun, Biesenthal-Danewitz (DE); Fraunhofer-Gesellschaft zur Foerderung der angewandten Forschung e. V., Munich (DE)

(72) Inventor: Trutz Podschun, Biesenthal-Danewitz (DE)

(73) Assignee: FRAUNHOFER-GESELLSCHAFT ZUR FOERDERUN DER ANGEWANDTEN FORSCHUNG E.V., Munich (DE)

( * ) Notice: Subject to any disclaimer, the term of this patent is extended or adjusted under 35 U.S.C. 154(b) by 115 days.

(21) Appl. No.: 16/040,650

(22) Filed: Jul. 20, 2018

(65) Prior Publication Data
US 2018/0326210 A1    Nov. 15, 2018

Related U.S. Application Data

(63) Continuation-in-part of application No. PCT/EP2017/050784, filed on Jan. 16, 2017.

(30) Foreign Application Priority Data

Jan. 20, 2016 (DE) .................. 10 2016 100 886

(51) Int. Cl.
*A61N 1/36* (2006.01)
*A61B 5/11* (2006.01)
(Continued)

(52) U.S. Cl.
CPC ........ *A61N 1/36014* (2013.01); *A61B 5/0488* (2013.01); *A61B 5/1121* (2013.01);
(Continued)

(58) Field of Classification Search
CPC .............. A61N 1/36014; A61N 1/0551; A61N 1/36031; A61N 1/36003; A61N 2/002;
(Continued)

(56) References Cited

U.S. PATENT DOCUMENTS

| 2002/0161415 A1 | 10/2002 | Cohen et al. |
| 2006/0292187 A1 | 12/2006 | Smith |

(Continued)

FOREIGN PATENT DOCUMENTS

| DE | 102006008495 A1 | 9/2007 |
| DE | 102009057962 A1 | 6/2011 |

OTHER PUBLICATIONS

International Search Report for PCT/EP2017/050784 dated Mar. 27, 2017; English translation submitted herewith (9 pages).

(Continued)

*Primary Examiner* — Rex R Holmes
(74) *Attorney, Agent, or Firm* — Fitch, Even, Tabin & Flannery LLP

(57) ABSTRACT

A system for regeneration of at least one severed nerve conduit, configured for use in a living human or animal body. The at least one nerve conduit comprises at least one motor nerve conduction part and at least one sensory nerve conduction part. The system comprises: a motion device, configured for moving a body part of the human or animal body, for containing at least one skeletal muscle that is otherwise innervatable with the at least one severed nerve conduit, a signal generator, which generates a first electrical stimulation signal and a second electrical stimulation signal, including an evaluation and control, which controls the motion device and the signal generator to be coordinated with one another.

19 Claims, 6 Drawing Sheets

(51) Int. Cl.

| | |
|---|---|
| *A61B 5/00* | (2006.01) |
| *A61F 2/72* | (2006.01) |
| *A61N 1/05* | (2006.01) |
| *A61B 5/0488* | (2006.01) |
| *A61H 3/00* | (2006.01) |
| *A61M 5/172* | (2006.01) |
| *A61N 2/00* | (2006.01) |

(52) U.S. Cl.
CPC .......... *A61B 5/4041* (2013.01); *A61B 5/4851* (2013.01); *A61B 5/6812* (2013.01); *A61F 2/72* (2013.01); *A61H 3/00* (2013.01); *A61M 5/1723* (2013.01); *A61N 1/0551* (2013.01); *A61N 1/36003* (2013.01); *A61N 1/36031* (2017.08); *A61H 2201/1207* (2013.01); *A61H 2201/164* (2013.01); *A61H 2201/165* (2013.01); *A61H 2201/5007* (2013.01); *A61H 2201/5043* (2013.01); *A61H 2201/5064* (2013.01); *A61H 2230/085* (2013.01); *A61M 2230/08* (2013.01); *A61N 2/002* (2013.01)

(58) Field of Classification Search
CPC . A61B 5/1121; A61B 5/4851; A61B 5/04888; A61B 5/6812; A61B 5/4041; A61F 2/68; A61F 2/72; A61H 3/00; A61H 2201/1207; A61H 2201/164; A61H 2201/165; A61H 2201/5007; A61H 2201/5043; A61H 2201/5064; A61H 2230/085; A61M 5/1723; A61M 2230/08

See application file for complete search history.

(56) References Cited

U.S. PATENT DOCUMENTS

| | | |
|---|---|---|
| 2011/0224665 A1 | 9/2011 | Crosby et al. |
| 2013/0060266 A1 | 3/2013 | Bretthauer et al. |
| 2013/0304174 A1 | 11/2013 | Langhals et al. |
| 2015/0057723 A1 | 2/2015 | Starobin et al. |
| 2015/0173918 A1* | 6/2015 | Herr .......................... A61F 2/72 623/25 |
| 2016/0302686 A1* | 10/2016 | Einarsson ................ A61F 2/60 |

OTHER PUBLICATIONS

Xavier Navarro et al: A critical review of interfaces with the peripheral nervous system for the control of neuroprostheses and hybrid bionic systems11 , Journal of the Peripheral Nervous System, vol. 10, No. 3, Sep. 1, 2005 (Sep. 1, 2005), pp. 229-258, XP055298492, ISSN: 1085-9489, DOI: 10.1111/i.1085-9489.2005.10303.x the whole document.

Alluin O et al: "Functional recovery after peripheral nerve injury and implantation of a collagen guide", Biomaterials, Elsevier Science Publishers BV., Barking, GB, vol. 30, No. 3, Jan. 1, 2009 (Jan. 1, 2009), pp. 363-373, XP025632723,ISSN: 0142-9612, DOI:10.1016/J.BIOMATERIALS.2008.09.043, [retrieved on Oct. 16, 2008] the whole document.

Decherchi P et al: "Electromyostimulation et recuperation fonctionnelle d'un muscle denerve" Science and Sports, Ed. Scientifiques Elsevier, Paris, FR, vol. 18, No. 5, Oct. 1, 2003 (Oct. 1, 2003), pp. 253-263, XP027514234, ISSN: 0765-1597, DOI: 10.1016/S0765-1597(03)00144-8 [retrieved on Oct. 1, 2003] the whole document.

* cited by examiner

SYSTEM AND METHOD FOR THE REGENERATION OF AT LEAST ONE SEVERED NERVE CONDUIT

CROSS REFERENCE TO RELATED APPLICATIONS

This application is a Continuation in Part of PCT/EP2017/050784, filed Jan. 16, 2017, which claims priority from German Application No. 10 2016 100 886.9 filed Jan. 20, 2016, which are incorporated herein by reference in their entirety.

BACKGROUND OF THE INVENTION

Field of the Invention

The invention relates to a system and method for regeneration of at least one severed nerve conduit in a living human or animal body. Such severed nerve conduits may be the result of a trauma, for example, as a result of an accident or an unsuccessful surgical procedure, a tumor in the central nervous system, an infection or an autoimmune disease, which is manifested, for example, in a failure of or at least a disturbance in conduction of nerve stimuli from the control centers (brain, spinal cord) to the target tissue in the periphery such as muscles or organs, and/or from back from there and results in a complete or at least partial function failure of the respective target tissue.

The nerve conduits running from the control centers to the peripheral target teachers are referred to below as "motor nerve conduction parts" and the nerve paths running back from the peripheral target tissues are referred to as "sensory nerve conduction parts."

Human motion sequences are complex processes taking place on three levels:
1. the anatomical/physiological level,
2. the functional level and
3. the cybernetic level.

Each of these levels in turn consists of a number of sublevels.

The Anatomical/Physiological Level
The most important fundamental part is formed by anatomical components of the body, the joints, muscles, tendons, nerve cells and nerves, with the nerves playing a special role because they transport cybernetic information in the form of nerve stimuli from one location in the body, a control center, to another location in the body, the element controlled, and then back again by means of physiological processes. These biological information conductors are similar to electrical lines or glass fibers in the industry.

Nerves consist of individual nerve fibers, the "incoming and outgoing lines" of a nerve cell (neuron). We recognize two basic types: first, neurites, i.e., cell projections which transfer a stimulus from the cell body to the end of the projection of the nerve cell ("efferent"), where it then is transferred to other nerve cells or muscles. If these lines are surrounded by an insulating layer of glial cells ("Schwann cells") like the plastic sheathing on electric lines, they are referred to as axons (see FIG. 6). Secondly, there are dendrites which serve to receive a stimulus from another nerve cell or a sensor cell and conduct it in the direction of the cell body ("afferent"). As a rule, a nerve cell has several dendrites but only one neurite or one axon. However, the length of the dendrites may vary greatly and may sometimes be as long as an axon (sensory nerve fibers of the spinal nerves) which in humans may be up to 1 meter long.

Neurites end in "synapses," i.e., contact-free connections between a nerve cell and another cell, e.g., another nerve cell or gland cells or muscle cells. The transition from a nerve fiber to a muscle fiber is often referred to as the "motor end plate." The stimulus is also received by dendrites via synapses.

If nerve cells serve to transfer instructions from the "central nervous system" to muscles or muscle groups "in the periphery," we speak of motor signals. The nerves which conduct them are known as "motor nerves," and their nerve cells are motor neurons and the nerve fibers are "motor nerve fibers." These are "type A, subtype α."

In addition, there are also nerve cells that conduct signals back into the central nervous system (sensory neurons) by successful conversion of a motor signal of the Aα type out of the periphery. From the standpoint of cybernetics, these sensory neurons are just as important as the motor neurons because they mediate feedback to the action. There are thus special anatomical structures in and on muscles, i.e., sensors, such as muscle spindles (MS) or Golgi tendon organs, which determine the contraction of a blood vessel and can provide information about the prevailing elongation status of muscle. These sensory signals are relayed by sensory nerve cells. A feedback mechanism formed from such motor nerve cells and sensory nerve cells is highly complex from the standpoint of control technology because the sensitivity of such sensors depends on the muscle elongation and must therefore be "readjusted" on the basis of the elongation status ("prestress"). There are other motor nerve cells (type A, subtype γ) for this task.

A nerve may have not only motor nerve fibers but also sensory nerve fibers. And a nerve may comprise different types of motor fibers (Aα and Aγ [muscles] and B and C [organs]) and sensory fibers (type Ia [muscle spindle], Ib [Golgi tendon organ], II [touch, pressure, vibration], III [temperature, "fast" pain; reflex triggering] or IV ["slow" pain; pain perception]). Nerves may belong to individual muscles or to muscle groups, in which case the nerve is then divided into different branches.

The Functional Level
The "motor cortex," i.e., the regions of the brain in the cerebral cortex where conscious and unconscious movements are planned, is the top functional level of movement. The lowest functional level then comprises the muscles, tendons and joints responsible for carrying out what is referred to as motion. In between there is the spinal cord, which can independently initiate movements (reflexes), but on the other hand, serves as an "interface" between the brain and muscles. This mediating level is particularly important for the present invention.

The functional level is implemented by biological feedback control systems. At the lowest sublevel, this is a simple "reflex arc." The best known example of such a reflex arc is the patellar tendon reflex. By tapping lightly on the patellar tendon with a reflex hammer, the skeletal musculature (S) is overextended briefly. This is picked up by a sensor in the muscle, known as the muscle spindle (MS). In response to the hyperextension, this spindle sends a signal from the muscle to the spinal cord via a sensory nerve. This sensory nerve represents half of a reflex arc. The second half is formed by a motor nerve. By stimulation of a motor neuron (of type α), a signal is transmitted to a skeletal muscle via a nerve-muscle connection known as the motor end plate, which causes the skeletal muscle to contract as a result and in response. Motor nerves thus "innervate" a muscle.

A simple feedback control system like the reflex arc is also used at the highest sublevel. A motor neuron here controls the activities of a motor neuron of a reflex arc to induce a muscle contraction. It receives feedback via a second sensory neuron, which in turn receives its information from the sensory neuron of the reflex arc or from another sensory source.

On a functional level, movement is the connection of at least two control systems to one another.

The Cybernetic Level

However, a movement cannot be carried out with these two levels alone. There is therefore a third level: the cybernetic level, consisting of a collection of information ("movement patterns") about when and which anatomical and physiological processes are to take place and in which order and how strongly and are to be executed by the functional control systems.

The cybernetic level is intangible. If anatomical, physiological and functional levels form the "hardware" of a movement, then the cybernetic level is the "software," which results in movement.

With these three subaspects of movement, the complexity of the process is represented only in simplified terms. Thus, in addition to the cerebrum and its motor sensors, motor nerve fibers and sensory nerve fibers and muscles, joints and sensors, other organs of the human body are also involved in the phenomenon of movement, e.g., the cerebellum, the main function of which is coordination and implementation of movement; this is the equilibrium organ or the spinal cord, which makes it possible to execute movements with the goal of getting the human being out of the dangerous situation as rapidly as possible in special life-threatening situations without requiring any intervention on the part of the brain.

The complexity of movement and the processes involved can be seen clearly by observing how human children learn to move. In particular, learning to walk is a tedious and complicated process because, in violation of the laws of mechanics, humans propel themselves on two legs and can stand on two legs vertically upright in a stable and reliable manner. Walking is in principle nothing other than a controlled movement of the center of gravity of a mass over a "stable" point, the position of the legs and feet. The start of a fall must be intercepted to prevent a fall. At the same time, the thrust that is necessary for this must first be generated and maintained until the movement is completed. If the speed at which the movement takes place is also to be altered, then the matter becomes even more complicated.

Standing is also not trivial. None of the joints involved has a locking mechanism to ensure stability. When standing, it is thus necessary to ensure that any deviations in joint positioning, regardless of the cause, are compensated accurately by muscle contractions, so as to result in no physical torque that might cause an unintended movement. Rigid immobility, when considered microscopically, is presumably a continuous sequence of micro-activities of muscles and joints. All of this is clearly apparent when one observes human children during the phase when they are learning how to stand, walk and run. It takes a long time accordingly for them to become agile in such activities.

Movement is the result of a learning process. Precisely this aspect is important. And like any learning process, what is learned is stored in the memory. This "movement memory" is controlled by the cerebellum, which accesses that memory unconsciously. Movement is thus predominantly an unconscious process even if it has been initiated consciously. One may consciously intend to stand up from the table and walk into the kitchen, and one may even initiate this, but what would then be necessary to implement this plan on a purely physical level is completely outside of our consciousness and our control. We do not know which muscles/muscle groups must be activated and relaxed, when and with which intensity, nor do we even know whether that actually takes place. We merely notice on the basis of our other sensory perceptions (eye, ear) that we are changing our position in accordance with our intent. We are not even conscious of information contributed by our positional and equilibrium organ.

Movement is thus a complex process based on saved movement patterns that were developed and optimized as part of a self-learning process during childhood. The complexity of this is also revealed in the effort we must make for even comparatively modest results to impart a human-like gait to a walking robot. Simple replacement of "hardware" in the form of stem cells, nerve cell transplantation or reactivation of compromised nerve cells and "simple" rehabilitation measures, such as those used today cannot achieve a cure because they do not repair the damage on an anatomical and functional level, while other levels are disregarded.

To restore movement after a paralysis or just a paresis, there must be a new learning process similar to that in childhood. This is the basis of the measures used so far in the context of rehabilitation. The problem from a cybernetic standpoint is that "repair" on an anatomical/physiological level and movement training are not coordinated and the particular details about feedback control systems are not taken into account: action and feedback. Another complicating factor is that, unlike during childhood, the basic anatomical and physiological prerequisites must be instilled anew in the context of the rehabilitation measure because they are not yet functionally reliable. Therefore, a suitable rehabilitation measure would be desirable.

Like anything that has been learned, movement can be learned again. Like school learning that one has not "used" in a long time, then was erased or at least displaced at some point in time, movement patterns can also be deleted or displaced again. Once that has happened, they must be replaced.

According to the complexity of movement, this process is also very complex because movement patterns that were once learned can then definitely be retrieved even after a long time of non-use (driving an automobile, "you never forget how to ride a bicycle," etc.). However, this is possible only if the type and sequence of cybernetic information that is stored in the movement pattern and is based on the anatomical and physical prerequisites have remained the same and can be employed with no problem. If that is not the case, for example, because nerves or muscles have been removed, the corresponding information has also been removed from the motion memory. This is apparent, for example, when procedures must be performed after a stroke or on the motor centers in the brain. In many cases here, patients must learn individual movements anew: the elements of self-learning systems through constant exercise and trial and error. In contrast with traditional rehabilitation measures, the movement patterns, the "software" here, is/are reconstructed ("programmed") on the basis of the functional control systems.

In summary, this means that the following are required for carrying out a movement on an anatomical level:

1. A control system on the lowest level, with which signals can be sent to muscles. This is achieved in humans and animals in the form of reflex arcs consisting of at least one motor nerve cell and one sensory nerve cell. First, the motor nerve cell ("second motor neuron," English:

lower motor neuron, LMN), whose cell body sits in the gray matter of the "motor anterior horn" in the spinal cord and its signal-transmitting nerve fibers, its "axon," leaves the spinal cord as part of a "spinal nerve" to enter the periphery of the muscle as a "nerve" together with the sensory nerve fiber and additional motor nerves and sensory nerves. Second, the sensory nerve cell whose cell body is settled on the exterior side as a "spinal ganglion" in the immediate vicinity of the spine. The sensor sitting on the muscle and/or tendon then transmits the feedback to this cell body via the sensory nerve fiber, which is formed here by dendrites of the sensory nerve cell and is part of the aforementioned "nerves." Its axon enters the spinal cord as part of the spinal nerve into the gray matter of the "sensory posterior horn." In the simplest case, it is now connected directly to the dendrites of the LMN, i.e., by means of only one synapse ("monosynaptic") but in many cases also indirectly with "interneurons" as the intermediary ("polysynaptic"). The control system is thus closed both anatomically and physiologically. "Reflexes," i.e., movements without any control or intent by means of higher movement centers, are possible by way of this control system. From an evolutionary standpoint, these are the most primitive motion sequences in vertebrates. These form the basis of all movement.

2. A feedback control system, by means of which these basic control systems according to point 1 can be influenced by the higher movement centers. This functions according to the same principle: there is a motor nerve cell (first motor neuron, English: upper motor neuron, UMN) in the brain, for example, in the motor centers of the brain that are responsible for movement. It sends its axon into the spine via the brain stem and the medulla oblongata. It is connected to the LMN there in a contact-free manner, via a synapse either directly or with the cooperation of reinforcing or inhibiting interneurons in between. The control system from point 1 can thus be controlled from the outside in this way.

This feedback control system also requires a sensory part for feedback. Therefore, there is also a sensory nerve cell here which establishes the connection between the control system in the spinal cord and the higher movement centers. It can obtain its information from two sources: either by the use of interneurons in connecting the components of the basic control system or by an additional sensory nerve cell, which also has its origin on a muscle and/or tendon but is not connected to the LMN and serves only to transfer information to and from higher centers (for example, "pain pathways").

"Efferent motor nerve fibers" from the upper motor neurons UMN and "afferent sensory nerve cells" from the "white matter" of the spinal cord. The motor nerve fibers here form the "pyramidal" and "extrapyramidal" pathways of the "anterior funiculus" and the "lateral white column of the spinal cord," while the sensory nerve fibers form the "posterior" and "anterior cerebellar tract."

The spinal cord is thus a complex system with its own intelligence ("reflexes"), although primitive, which can be utilized from the outside for targeted movements via the nerve connections to the brain.

Paresis ("paralysis") is a condition that occurs after injury to nerve pathways as a result of trauma, unsuccessful surgical procedures (e.g., correction of a herniated disk), a central nervous system tumor or destruction of nerve tissue due to an infection or an autoimmune disease (e.g., multiple sclerosis), which is manifested in a disturbance in or even a failure of conduction of nerve stimuli from the control centers (brain, spinal cord) to the target tissue in the periphery (motor, skeletal muscles, muscles of the urinary bladder and rectum), to organs (autonomous: urinary bladder, rectum, cardiovascular system) and from there (sensory) and results in a complete loss of function ("paralysis") of the respective target tissue. It is ultimately based on partial or complete destruction of at least one involved nerve cell and/or its projections, so that the control system and/or its control is/are functionally and physiologically interrupted from the higher level brain sensors.

The location of this destruction plays a crucial role here. Modern medicine today is often able to surgically restore peripheral nerves, i.e., the motor and sensory nerve fibers of such control systems, in the periphery. This is the basis of successful re-transplantation of severed limbs after neurosurgical operations. Sensory perceptions can often be restored after peripheral sensory nerve paths have been severed, e.g., in fractures. This often occurs spontaneously because the body has the ability to reconstruct nerve paths when the respective nerve cells are otherwise still largely intact. However, this requires suitable stimulation of the corresponding nerve cell and an otherwise intact environment in which the regeneration can take place without being disturbed.

However, this is possible more rarely, the closer the damage is to the spine, and it is practically impossible, at least from a neurosurgical standpoint, when it occurs in the spinal cord. In particular, the destruction of the lower motor neuron but also the capping of the connection between the UMN and LMN usually result in an irreparable "denervation" of the muscles or muscle groups innervated by the LMN. The result is paralysis of individual muscles or muscle groups with the effect that no movement is triggered (or can be triggered). Paralysis of entire extremities or portions of limbs therefore occurs in "transverse lesion paraplegia."

Due to the great importance of the pyramidal and extrapyramidal pathways of the spinal cord (connections between the UMN and LMN), paralysis also occurs when there is damage to the motor cortex (cerebral and/or cerebellar cortex). Damage to the nerves of the brachial plexus (network of various spinal nerves of the cerebral and thoracic regions [C4-Th2], innervating the upper extremities and the thoracic wall) and the lumbosacral plexus (network of various spinal nerves of the lumbar and sacral regions [Th12-S5], innervating the lower extremities, the abdominal wall and the pelvis) can also result in failure of some muscle groups.

The following forms of paralysis have been identified on the basis of the symptoms following such nerve damage:
  monoplegia: complete paralysis of one extremity or a portion of an extremity (e.g., forearm)
  hemiplegia: complete paralysis of half of the body
  paraplegia: complete paralysis of the upper or lower extremity
  tetraplegia: complete paralysis of all extremities Which of these forms occurs after damage to neural tissue is defined by the location where occurs. The loss phenomena thus increase from caudally ("lower" in humans) to cranially ("toward the head"). Damage to the cervical spine immediately in the vicinity of the first cervical vertebrae can lead to tetraplegia, the most severe form of paralysis, because this is where the entire spinal cord below the head is severed from controlling pulses from the brain, so that no muscles of the body are innervated any longer. If the "transverse section" of damage is located lower (caudally), this is commonly known as "transverse paralysis"; then the patient may still be able to move his shoulders, the upper body together with the hands and arms or even the torso above the pelvis. If the damage is higher ("cervical fracture"), this is usually inconsistent with life because it includes paralysis of the respiratory muscles.

Paralysis is thus a highly individual condition that cannot be treated adequately by using standardized methods. Depending on the cause, individual characterization, localization and severity of the injury as well as the physical and psychological condition of the affected patient, different treatment methods must be used, possibly in combination with one another. An essential factor, which is often underestimated here, is the patient's psychological attitude. The patient must have the will to overcome the condition.

The situation becomes complicated when the site of the injury is close to or, in the worst case, inside the spinal cord. Neurosurgical procedures in or on the spine, in which individual nerve pathways can be restored, are practically impossible according to the latest research. This is the reason why paralysis conditions have so far been considered incurable and the medical treatment has consisted only of improving the patient's quality of life. This is done by establishing the maximum mobility that is physically possible according to today's standard through suitable rehabilitation measures. The remaining disability is then compensated as well as possible with technical medical options, including walking aids, wheelchairs and exoskeletons, but also orthotic devices or stimulus current generators, which carry out partial motion sequences by measuring when a "higher-level" muscle contraction occurs, and then stimulating another muscle after a suitable time lag or having the additional movement carried out by the orthotic device (e.g., dorsiflexion orthotics, FES—functional electrostimulation).

Supported by findings from recent scientific disciplines such as cellular biology, biochemistry and biotechnology and based on advances in neurosciences (functional imaging methods), attempts have been made for several years to adequately treat paralysis by ensuring restoration of the affected control system. This has led to the methods developed so far to prompt existing injured nerve cells to sprout again in the direction of the target tissue through the use of messenger substances and growth factors and to thereby replace the compromised nerve fibers. However, based on recent findings, so-called groundbreaking cells, such as olfactory supporting cells that should help the nerve cells find their way into the target tissue, have recently also been used here. Some of these experiments have been successful but they have not yet yielded the expected breakthrough.

Other approaches are aimed at replacing the damaged nerve cell with a new one. This takes place in particular when the original cell can no longer be reactivated—because it has been irreparably destroyed or because the time between injury and therapeutic measures is too long. Stem cells capable of differentiating to nerve cells under suitable conditions and in a suitable environment are used for this purpose. Alternatively, other nerve cells have also been transplanted. The goal is to restore the anatomical and physiological prerequisites for an intact control system. This has already been possible in individual cases, but here again, no pioneering success has yet been achieved.

The reason is that such a "repair" does not do justice to the anatomical and physiological prerequisites. The control systems must be functionally restored and maintained, which means that the interaction between action (motor pulse) and reaction (sensory feedback) must be restored. However, this can only take place a relatively long time after the surgical procedure, if at all. Nerve fibers must first grow (back) into the target tissue and the synaptic connections within the reflex arc itself but also with interneurons, and the higher brain centers must be restored, etc.

Whether the damage can be corrected functionally at all after such a procedure and, if so, to what extent depends significantly on the function of the reflex arc in question being maintained over the period of time until the physiological prerequisites have again been met. The natural functioning of the reflex arc must therefore be simulated as much as possible.

In the past, patients who had suffered an injury/severing of a nerve conduit or transverse paralysis had to be treated with auxiliary means such as wheelchairs, orthotic devices or artificial exoskeletons.

Examples include orthotic devices that are used for stroke patients who can no longer raise their foot/feet on their own. Known orthotic devices have electrodes for stimulating the muscles responsible for lifting the foot while walking.

Artificial exoskeletons are external supporting structures that may be designed purely mechanically but may also be considered to be robotic devices that are worn on a person's body and support and/or reinforce the movements of the wearer, for example, by the fact that joints of the exoskeleton are driven by servo motors. Such exoskeletons are used, at least in studies, for rehabilitation of patients with paralysis.

Although the aforementioned devices permit better management of everyday life, they are still not suitable for achieving regeneration of a severed, damaged nerve conduit.

Another approach for improving the quality of life of paralyzed people or those who have lost a hand or an arm, for example, and must rely on an orthotic device or a prosthesis is disclosed in DE 10 2006 008 495 A1. According to this innovation, the ability of the patient to move should be improved by the fact that the patient is controlling, through his will, his own body part, which is generally referred to as an effector, or a prosthesis. To do so, an electrode is provided by means of which the signals from an area of the brain responsible for the intended movement are detected, these signals being generated in preparation, planning, execution or control of a movement. The signals are classified and used, for example, to generate signals for functional stimulation of one's own body parts when the neural connection to the brain has been interrupted. Transmission of feedback from the body part back to the brain is also possible in that sensor signals, for example, intact endogenous pressure or strain receptors or signals from artificial sensors are sent back to the brain as stimulation data.

US Patent 2015/0057723 A1 and German Patent DE 10 2009 057 962 A1 each disclose a system for treatment of a severed nerve conduit by means of electrical stimulation.

However, there is no known state-of-the-art system that permits not only functional support of a patient but also regeneration of a severed nerve conduit and "repair" on a cybernetic level.

SUMMARY OF THE INVENTION

The invention is based on providing a system for regeneration of at least one severed nerve conduit in a living human or animal body, i.e., the system should serve not only as an aid for managing everyday life, in particular for paraplegic patients, but instead should also serve to regenerate the severed nerve conduit, with the goal of being able to eliminate the need for assisting devices in the long run.

The system according to this approach for regeneration of at least one severed nerve conduit in a living human or animal body has a motion device, with which it is possible to move a part of the human or animal body having at least one skeletal muscle that could otherwise be innervated with the severed nerve conduit. In addition, the system according to this approach has a signal generator unit, which generates a first electric stimulation signal and a second electric stimulation signal. Furthermore, according to this approach, an evaluation and control unit, which controls the motion device as well as the signal generator unit, so they are coordinated with one another, such that the signal generator unit applies the first stimulation signal via a first applicator to the nerve conduction part separated from the skeletal muscle and in chronological coincidence therewith, the motion device moves the body part. According to this approach, the signal generator unit applies the second stimulation signal to the nerve conduction part separated from the skeletal muscle by use of the first applicator or a second applicator at a time during or after the movement of the body part.

The second stimulation signal is applied in particular in such a way with a time lag from the first stimulation signal that the chronological sequence of the corresponding natural signals is simulated. The stimulation signals are selected with respect to their amplitude and signal form, such that they act on the corresponding nerve conduit to produce signals resembling the natural signals on this nerve conduit in intensity and form.

Due to the fact that the nerve conduit has been severed, the portion of the nerve conduit that is no longer directly connected to the skeletal muscle is referred to as being separated from the skeletal muscle. In particular, this portion of the nerve conduit contains the motor and/or sensory nerve conduction part separated from the skeletal muscle.

In the sense of this invention, the portion of nerve conduit that conducts signals emanating from the brain and/or spinal cord for triggering the skeletal muscle is to be interpreted as a motor nerve conduction part.

Accordingly, the sensory nerve conduction part in the sense of the present invention should be interpreted as that portion of the nerve conduit that conducts signals, which emanate from the skeletal muscle or from biological sensors in functional contact with the skeletal muscle and should reach the spinal cord or the brain. Nerve signals emanating from the skeletal muscle are to be understood as signals generated by contraction or elongation of the muscle, for example, from the muscle spindles or the Golgi tendon apparatus.

Fundamentally, neurons can be stimulated only by nerve signals arriving at their dendrites. Therefore, the site of application of the first stimulation signal must be selected, so that an artificial nerve signal generated by the stimulation signal will reach at least one dendrite of the last neuron before the physical interruption and/or severing point of the motor nerve conduction part and will thereby stimulate this neuron.

The situation is similar for the application site of the second stimulation signal. The second stimulation signal can be applied here only to the dendrites of the first neuron, which is located after the physical interruption and/or separation point.

The advantage of the system according to this approach is the fact that the neuron situated closest to the separation point is stimulated to grow back into the region no longer supplied based on the severed nerve conduit, by stimulation of the motor nerve conduction part separated from the muscle with the first stimulation signal and by the feedback in the form of the second stimulation signal. Based on the motor nerve conduction part, this means growth in the direction of the skeletal muscle because the cell body that is the actual "cell" and therefore can prompt growth and can implement growth is located in the motor anterior horn of the spinal cord. Growth therefore takes place along the motor nerve conduction part, always in the direction of the skeletal muscles. The sensory nerve cells here are a special form of nerve cells, the so-called pseudounipolar nerve cells, in which the cell body as the spinal ganglion is in direct contact with the spine. In this case, the dendrite to the skeletal muscle is a long projection, while the axon into the spinal cord is very short. Therefore, in the case of a severed nerve, the dendrite, which also grows in the direction of the skeletal muscle, must grow here.

It is also conceivable to prompt a nerve pathway and/or nerve cell, which has been implanted in the area of the severed nerve and has been restored externally but has not yet become functional again, to integration by stimulation of the motor nerve conduction part, so that the previously severed nerve conduit is regenerated.

The signal generator unit preferably generates a third electrical stimulation signal which can be applied to the skeletal muscle by a third applicator. The evaluation and control unit is designed to control the signal generator unit, so that the third stimulation signal is applied to the skeletal muscle simultaneously with the first stimulation signal or while the motion device has been moving the body part. Direct stimulation of the skeletal muscle by use of an applicator placed there or indirect stimulation of the skeletal muscle by stimulation of the part of the motor nerve conduction part that is still connected to the muscle and still functional are possible by stimulation of that part that is still functional, is still connected to the muscle and leads to the muscle. In particular, the three stimulation signals as well as the movement by the motion device are coordinated with one another, so that the movement can be stimulated with their natural nerve signals belonging there in a healthy patient, to thereby promote regeneration of the severed nerve conduit. The extent, in particular the amplitude of the stimulation of the skeletal muscle, is preferably also adapted to the movement of the body part mediated by the motion device.

The system especially preferably has an injector system, which can also be controlled by the evaluation and control unit and applies at least one active ingredient in the area of the severed nerve conduit. The active ingredients are preferably applied in the region of the cell bodies of each neuron, which are adjacent to the interruption and/or were applied in the region of the interruption to restore the nerve conduction in order to prompt it to at least one of growth and to integration and thereby contribute to regeneration of the nerve conduit. In particular, specific nerve growth factors or messenger substances may be injected to promote nerve growth, for example, the growth of new axons, but also the integration of implanted nerve cells. Alternatively, active ingredients, which stimulate the stem cells to differentiate in the case of stem cell therapy for physical restoration of the nerve conduit, can also be injected. The evaluation and control unit is preferably designed so that it can control the dispensing of the active ingredients in both time and quantity by the injector system.

In another preferred embodiment, the system comprises at least one memory unit for storing data, on the basis of which the evaluation and control unit controls the motion device and the signal generator unit and especially preferably also the injector system. In particular, data in the form of different data records can be saved in the memory unit, wherein the data characterizes at least one movement and movement patterns that are and/or can be adapted specifically to the patient by using stimulation signals and/or administration of active ingredient(s) appropriate for the patient or the movement (pattern).

It is preferable for at least one of the first applicator and for the second applicator to have an electrode array. The electrode arrays are connected directly or indirectly to the signal generator unit and are designed to conduct electrical currents or for generating electrical, magnetic or electromagnetic fields. The first applicator may be designed so that both the first and second stimulation signals can be applied by use of it. In this case, an electrode array having at least two electrodes is recommended, wherein at least one of the first and second stimulation signal(s) can be applied via one of the at least two electrodes.

However, it is also possible for the first stimulation signal to be applicable via the first applicator and for the second stimulation signal to be applicable via the second applicator. In this case, the corresponding electrode arrays may each comprise only one electrode.

The electrodes themselves may be embodied in the form of electrodes that can be placed on the skin. Alternatively, the electrodes may also consist of a combination of an implanted electrode and a surface electrode placed on the skin, wherein the implanted electrode produces direct stimulation of the motor or sensory nerve conduction part and is connected wirelessly, for example, to the surface electrode, which is in turn connected to the signal generator unit.

The third applicator preferably also has an electrode array for moving the skeletal muscle to contraction by use of electrical signals. The elongation of the skeletal muscle is achieved by stimulation of the "counterpart" belonging to the skeletal muscle, that is, when the counterpart is moved to contract. Stimulation of the skeletal muscle may take place, for example, in the form of a stimulus current by use of one or more electrodes that can be applied to the skin over the muscle or by use of stimulation of the motor nerve conduction part leading to the skeletal muscle.

The motion device preferably has as orthotic device or an exoskeleton. The exoskeleton may be a partial skeleton, with which only a paralyzed body part, e.g., an arm or a leg, is moved, as well as a complete exoskeleton. Such an exoskeleton may also have a supporting function, in addition to just having a movement function, that is, the exoskeleton may take on additional functions, such as relieving the weight of the body or body parts or maintaining equilibrium. A complete exoskeleton can thus enable a person to walk upright.

The evaluation and control unit and at least one of the signal generator unit and the memory unit is/are preferably arranged on the orthotic device or the exoskeleton and form an independent unit. It is also preferable for a power supply unit, in the form of a rechargeable battery unit, to be arranged on the orthotic device or the exoskeleton in order to allow free mobility without restriction due to cables or tubing. Alternatively or additionally, a power supply unit that is separate from the motion device may also be provided. In the case of a separate power supply, for example, electrical or pneumatic, the power may be transferred to the motion device by means of lines and/or tubing.

The motion device preferably has at least two components connected to one another by use of a joint as well as at least one actuator by use of which the components can be moved relative to one another. The at least one actuator can be controlled by use of the evaluation and control unit. For example, at least one of linear drives and rotary drives may be considered as the actuators. In particular, at least one rotary drive and one joint may be integrated into a unit.

The system especially preferably has a motion sensor system, which is provided on the motion device and detects the relative spatial position of the components. The motion sensor system may be an integral part of at least one of the joint and actuator, for example, and may detect the condition of at least one of the joint and the actuator, for example, by use of corresponding generator sensors (angle sensor, rotary position transducer, position sensor, etc.). Alternatively or additionally, the motion sensor system may also have optical sensors for detecting the relative spatial position of the components. In any case, the motion sensor system generates at least one first motion sensor signal which can be evaluated by use of the evaluation and control unit that is connected directly or indirectly to the motion sensor system so that at least the relative spatial position of the components can be determined.

The system can especially preferably be used in an operating condition in which the motion device can be moved without support by at least one of the actuator and without control by the evaluation and control unit, wherein the evaluation and control unit generates motion data in this operating state based on the initial motion sensor signals generated by the motion sensor system and stores the data in the memory unit. This operating condition, in which the motion device can be moved more or less while idling serves to generate motion data corresponding to the natural motion sequence carried out by the body part in (natural) stimulation of at least one skeletal muscle. One possibility for obtaining such motion data applies the motion device to a healthy person, who then carries out the desired motion sequence. The evaluation and control unit then generates motion data from the relative spatial positions of the at least two components detected by use of the motion sensor system, wherein such motion data can be stored in the memory unit. Alternatively, the motion device may also be applied to the patient, and the corresponding body part may be moved passively in accordance with the desired motion sequence, wherein the motion data is again obtained by use of the motion sensor system and the evaluation and control unit. This motion data can then serve as the basis for the data used by the evaluation and control unit to control the motion device as well as the signal generator unit during normal operation.

The motion sensor system preferably also detects at least one of forces and torques occurring on the motion device during the movement and generates at least one second motion sensor signal that is comparable to reference data by a comparator unit. The comparator unit is designed so that it generates a signal when there is a deviation between the at least one second motion sensor signal and the reference data exceeding a predetermined threshold and sends this signal to the evaluation and control unit that is connected to the comparator unit and evaluates the signal. The cause of at least one forces and torques that may result in motion sensor signals deviating from the reference data may originate from the regenerating nerve conduit, for example. In this case, for example, new data may be used as the basis for controlling the system, thereby reducing the extent of support/passive movement of the patient by at least one of the exoskeleton, the orthotic device, reducing the extent of stimulation of the motor, sensory nerve conduction parts and the skeletal muscle to the extent that regeneration of the nerve conduit progresses. On the other hand, however, the signal may also indicate a need for repair of the system.

In another preferred embodiment of the system, a detector unit is provided, detecting electrical brain signals and generating a detector signal that is transmitted to the evaluation and control unit connected to the detector unit. The evaluation and control unit evaluates the detector signal and controls the motion device as well as the signal generator unit in accordance with data stored in the memory unit. In particular, it should be possible to detect a hypnotic state of the brain while a predetermined motion sequence is being executed using the respective stimulation signals.

In another preferred embodiment, a sensor system, which detects a quantifiable change in state in the motor nerve conduction part, the sensory nerve conduction part, the skeletal muscle and/or the body part, is detected and generates a sensor signal. The sensor system is connected to the evaluation and control unit which evaluates the sensor signal. It serves in particular to detect incipient regeneration and/or improvement in the nerve conduction in order to provide, for example, new data for triggering the control unit in accordance with progress, in which the supply of external stimuli, external support of the patient by means of the motion device and/or administration of active ingredients by means of the injector system is/are scaled back/adapted in accordance with regeneration results. This new data can be generated by the evaluation and control unit or by a new learning phase. Additional details can be found in the discussion below.

The goal is to be able to successively omit the exoskeleton and/or the orthotic device and the external stimuli.

The evaluation and control unit especially preferably has an interface, which the evaluation and control unit can be connected to at least one of the external memory unit, at least one external evaluation and the control unit in a hardwired or wireless connection. The advantage is that in the case when the system is designed as an independent unit in particular, it can be designed to be as lightweight as possible. In particular, computational power, which does not directly serve the function of control of at least one of the motion device, the signal control unit and data that need not necessarily be stored in the local memory unit, can be outsourced. In particular, external (expert) knowledge from other patient data, experiments, comparative cases or the patient's other data records, for example, can be stored in an external database. The external evaluation and control unit makes it possible, for example, to generate new data records or to verify data records, for example, from the external database, for at least one of concrete applicability and suitability for the patient.

It is especially preferable that a first sensor unit is provided, detecting a natural electrical nerve signal intended for stimulating the skeletal muscle and generating at least one sensor signal. The first sensor unit is connected to the evaluation and control unit, which evaluates the first sensor signal and controls the signal generator unit on the basis of the first sensor signal evaluated for generating the third stimulation signal. This permits artificial simulation of the interrupted/severed nerve conduit, in particular the part provided for control of the muscle. The signals detected by the first sensor unit are preferably filtered by at least one filter to isolate the natural nerve signal serving the purpose of control from the noise and other interference signals also detected and, if possible, to process this filtered-out isolated signal by means of a signal processing unit, so that a third stimulation signal corresponding to the natural nerve signal can be generated by the signal generator unit. Both random nerve signals running from the brain along the spinal cord and reflex signals running inside the spinal cord to the lower motor neuron are included here as the natural electrical nerve signal intended for stimulating the skeletal muscle.

In another preferred embodiment, a second sensor unit is provided, detecting an electrical nerve signal of the sensory nerve conduction part connected to at least one of the skeletal muscle and detecting activity of the skeletal muscle and then generating at least one second sensor signal. The second sensor unit is connected to the evaluation and control unit, which evaluates the second sensor signal and controls the signal generator unit on the basis of the second sensor signal thereby evaluated to generate the second stimulation signal. This makes it possible to simulate nerve conduction, so that nerve signals are conducted from the muscle to at least one of the spinal cord and the brain. It is also preferable here for the evaluation and control unit to comprise corresponding filters and signal processing units, which are necessary for generating a suitable second stimulation signal.

The first and second sensor units can be used to simultaneously also detect the respective natural stimulation signals in the case of an external movement of the motion device in the context of obtaining motion data. Then, by use of the evaluation and control unit, the stimulation data corresponding to at least one of the motion data for the motor nerve conduction part, the sensory nerve conduction part and the skeletal muscle can be determined by the evaluation and control unit, so that a complete set of data can be generated.

The evaluation and control unit is connected at least to the motion device and the signal generator unit. The evaluation and control unit is optionally connected to the injector system. The signal generator unit is in turn connected to the first and second applicators and optionally to the third applicator. A connection permits at least one of hardwired and wireless transmission of signals.

Based on the before described system, an inventive method for regenerating at least one severed nerve conduit in a living human or animal body which contains a body part having at least one skeletal muscle that would otherwise be innervatable with the severed nerve conduit can be performed by the following method steps:
  generating a first electrical stimulation signal;
  applying the first electrical stimulation signal to a nerve conduction part separated from the skeletal muscle (S) of the severed nerve conduit;
  moving the body part in chronological coincidence with application of the first electrical stimulation signal to the nerve conduction part separated from the skeletal muscle;
  generating a second electrical stimulation signal; and
  applying the second electrical stimulation signal during or after the movement of the body part on a nerve conduction part that is separated from the skeletal muscle.

In a preferred embodiment of performing the method, the first electrical stimulation signal is applied to the motor nerve conduction part, and the second electrical stimulation signal is applied to the sensory nerve conduction part.

In addition or alternatively to the before embodiment of performing the method a third electrical stimulation signal is generated, and the third electrical stimulation signal is applied to the skeletal muscle simultaneously with the first stimulation signal or while carrying out the movement of the body part.

In addition or alternatively to one of the before embodiments of performing the method during or after application of the at least one of first and second electrical signals an active ingredient is applied in the area of the severed nerve conduit.

BRIEF DESCRIPTION OF THE INVENTION

The invention is described below on the basis of exemplary embodiments with reference to the drawings as an example, without restriction of the general inventive idea of the invention, in which.

DETAILED DESCRIPTION OF THE INVENTION

Figure 1:
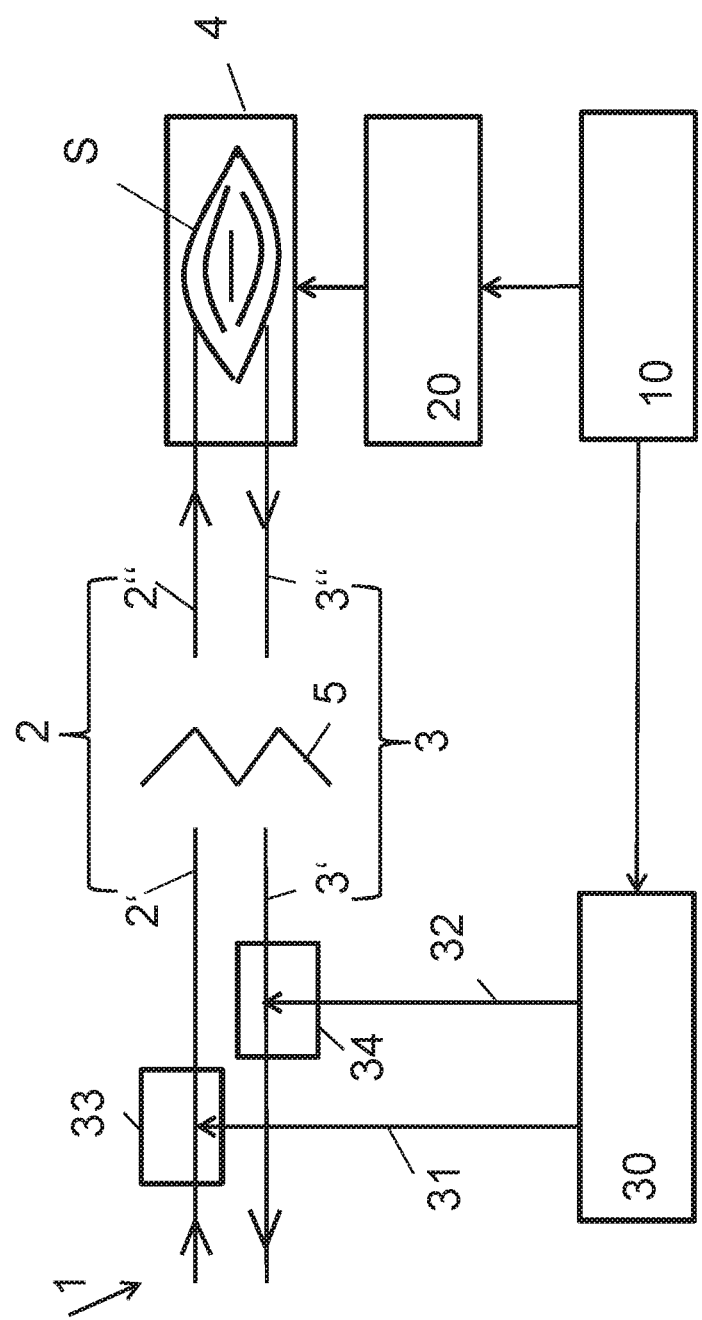
FIG. 1 shows a schematic diagram of one embodiment of the system according to the invention.

FIG. 1 shows a greatly simplified schematic diagram of a severed nerve conduit 1 having a separation point 5. The term separation point 5 need not necessarily be understood to refer to the location of a lesion in the narrower sense, but instead this refers to a region of a functional interruption in or disturbance of nerve conduction, along which at least there is irritation in the nerve signal transmission, by use of which the natural nerve signal transmission is disturbed. The nerve conduction 1 comprises a motor nerve conduction part 2 and a sensory nerve conduction part 3, which originally innervated the skeletal muscle S, that is the skeletal muscle S was stimulated to contraction by the motor nerve conduction part 2 and the signals generated by the muscle, for example, by at least one of a muscle spindle and at least one Golgi tendon apparatus are conducted via the reflex arc back to the spinal cord and from there to at least one of the brain H and to the corresponding lower motor neuron as the feedback signal which indicates contraction.

At least one of the motor nerve conduction part 2 and the sensory nerve conduction part 3 are each divided into a nerve conduction part 2', 3' separated from the skeletal muscle S and a nerve conduction part 2", 3" connected to the skeletal muscle. This division is accomplished by the separation point 5, which represents a functional interruption. Therefore, nerve signals that should be transmitted over the motor nerve conduction part 2 to the skeletal muscle S no longer arrive there. Accordingly, the sensory nerve conduction part 3' which is separated from the skeletal muscle S also no longer receives feedback signals from the skeletal muscle S, for example, from at least one of the muscle spindle and/or from the Golgi tendon apparatus, so that neither the spinal cord (including the lower motor neuron) nor the brain is "informed" about contraction of the skeletal muscle S and the associated movement.

Interruption of this closed system can lead to a further regression of at least one of nerve conduction and loss of arbitrary control, that is the ability of the brain to transmit nerve signals suitable for initiating a muscle movement.

The invention described below is based on the finding that a damaged neuron, which should grow back into at least one of the separated region, and a restored or prepared nerve connection that is to be integrated, requiring a stimulus to do so.

The system according to the invention begins at this point. This enables movement of the body part in combination with nerve stimulation signals, which correspond to those that naturally correlate with the movement of the body part, in particular with the contraction of the skeletal muscle S. Accordingly, the system according to the invention has a motion device 20 that moves the body part in question and a signal generator unit 30 generating a first stimulation signal 31 and a second stimulation signal 32. The first stimulation signal 31 is applied by the first applicator 33 to the motor nerve conduction part 2' separated from the skeletal muscle S, wherein the first stimulation signal 31 is designed in amplitude and signal form in particular, to generate a nerve signal along the motor nerve conduction part 2' separated from the skeletal muscle S, corresponding to the natural nerve signal occurring there for arbitrary or non-arbitrary control of the skeletal muscle S. The last neuron before the separation point, in particular its dendrites, is/are therefore stimulated artificially. The second stimulation signal 32 is also applied to the sensory nerve conduction part 3' separated from the skeletal muscle S either also via the first applicator (see FIG. 2) or via a second applicator 34 (see FIG. 1). In doing so, the dendrites of the neuron of the sensory nerve conduction part, which are closest to the separation point and from which the nerve signal generated artificially by use of the second nerve stimulation signal is relayed as a feedback signal in the direction of at least one of the spinal cord and the brain, are to be regarded as the first suitable site for stimulation. In this way, ultimately the last neuron of the motor nerve upstream from the separation point 5 receives a feedback signal via the detour of at least one of reflex arc and the spinal cord— brain—spinal cord pathway.

The system according to the invention also has an evaluation and control unit 10, which is connected to and controls the motion device 20 and the signal generator unit 30, so that the first stimulation signal 31 is applied in chronological coincidence with the movement of the body part 4 carried out by the motion device 20, and the second stimulation signal 32 is applied during or after the movement of the body part 4. However, the second stimulation signal 32 is at least offset in time from the first stimulation signal 31, as is also the case in the natural system.

Figure 2:
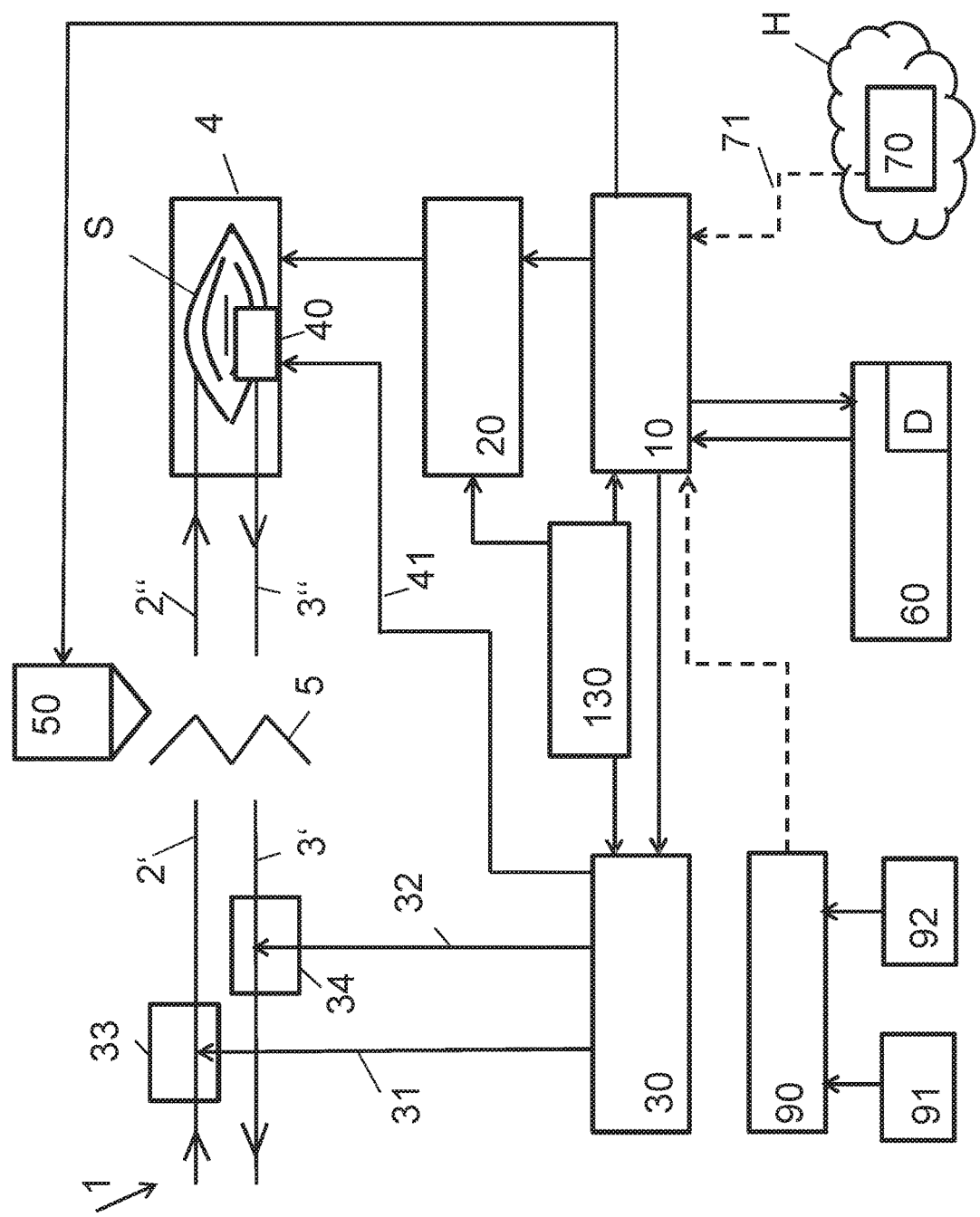
FIG. 2 shows a schematic diagram of a preferred embodiment of the system according to the invention.

Besides the above-mentioned variant according to the invention for application of the second stimulation signal 2 via the first applicator 31, FIG. 2 also shows additional preferred refinements of the system. These include a third applicator 40, by which a third electrical stimulation signal 41 which is generated by the signal generator unit 30 can be applied to the skeletal muscle S. In doing so, the third applicator 40 can stimulate the skeletal muscle S directly, as indicated in FIG. 2, to excite it to contraction, or stimulate it indirectly, by stimulation of a part of the motor nerve conduction part 2" (not shown) that is still connected to the skeletal muscle and is still functional. In doing so the evaluation and control unit 10 controls the signal generator 30, so that the third stimulation signal 41 is applied to the skeletal muscle S simultaneously with the first stimulation signal 31 or while the motion device 20 is moving the body part 4. "Simultaneously" means that, in any case, a possible time lag between stimulation of the skeletal muscle S and of the motor nerve conduction part 2' separated from the skeletal muscle S corresponds to the natural transit-time-related time lag and optionally to its biological processing time.

FIG. 2 also shows an injector system 50, by which active ingredients can be administered in the area of the severed nerve conduit 1. The application site is preferably to be selected, so that the active ingredients can be absorbed by the neurons and/or cells, which should be stimulated to at least one growth and to integration. The injector system 50 is preferably connected to the evaluation and control unit 10 and can be controlled by use of it, in particular it is possible to influence the release of active ingredients in both time and amount. Thus, for example, the nerves send out their projections on the basis of the gradients of certain messenger substances, that is, it may easily become necessary to apply certain growth factors directly to the damaged site but also to the target region. Application of at least one of the active ingredients and/or growth factors directly to the cell body may be appropriate.

FIG. 2 also shows a preferred memory unit 60, in which data D is stored on the basis of which the evaluation and control unit 10 controls the motion device 20 and the signal generator unit 30. Data D preferably comprises motion data BD for controlling the motion device as well as stimulation data SD for controlling the signal control unit which in turn generates at least one first stimulation signal 31, one second stimulation signal 32 and one third stimulation signal 41 in accordance with the stimulation data. Likewise, data D may also include data ID relating to the release of the active ingredient via the injector system. Motion data BD, stimulation data SD and, optionally, injector system data ID form the data record. A plurality of such data records may also be stored in memory unit 60.

FIG. 2 also indicates a power supply unit 130, which supplies power at least one directly and indirectly to the system components, that is evaluation and control unit 10, motion device 20, signal generator unit 30, injector system 50 and memory unit 60.

FIG. 2 also illustrates as a preferred embodiment a detector unit 70, designed to detect electrical brain signals and generate a detector signal 71, which is evaluated in evaluation and control unit 10 connected to detector unit 70. Evaluation and control unit 10 is designed to control the motion device 20 and the signal generator unit 30 as a function of detector signal 71, which is evaluated in accordance with data D stored in memory unit 60. Detector unit 70 in particular is designed, so that a hypnotic brain state is detected, and a predefined movement is carried out by the motion device 20 during the hypnotic state.

Figure 3:
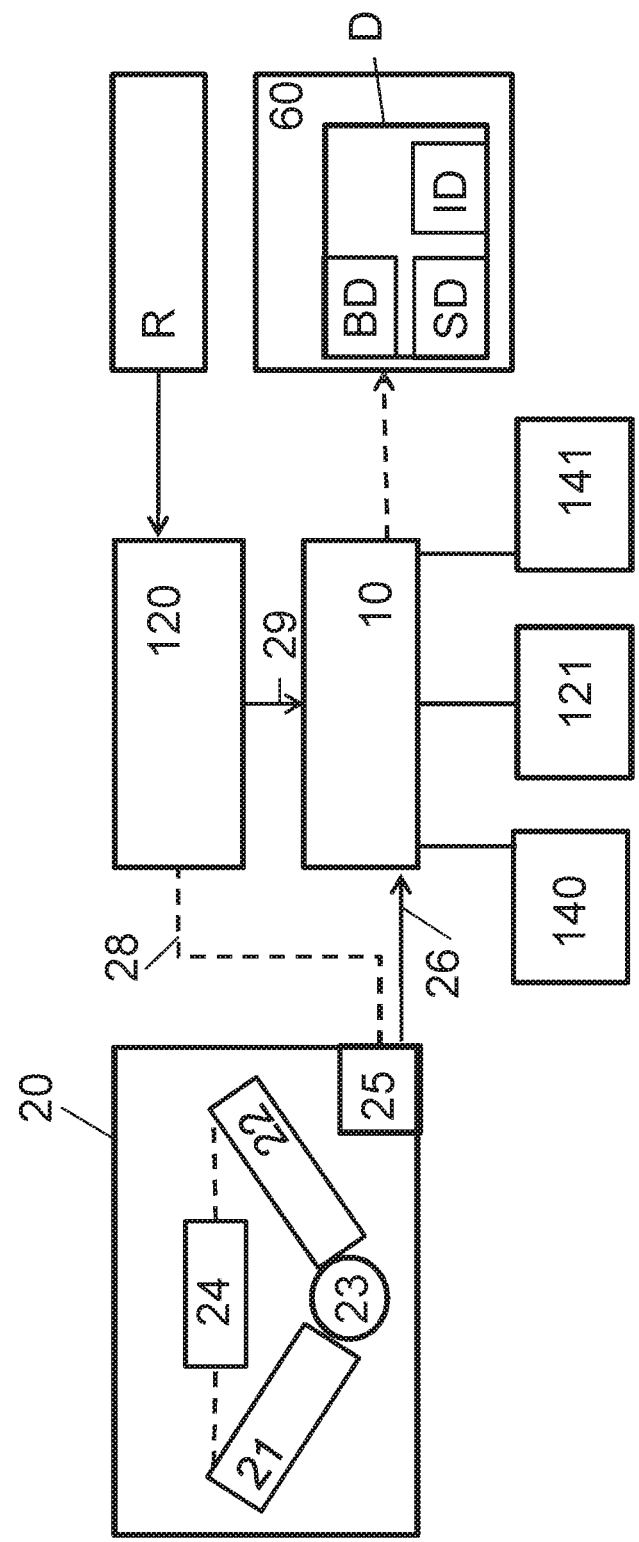
FIG. 3 shows a schematic diagram of a simple motion device.

FIG. 3 shows schematically a motion device 20 having two components 21, 22 connected to one another by a joint 23. The components 21, 22 are movable relative to one another by the actuator 24, wherein the actuator 24 can be controlled by the evaluation and control unit 10 according to the predetermined motion data. Motion device 20 may have substantially more components 21, 22 that are movable relative to one another, each with the respective actuators 24. In particular, a complete exoskeleton has a plurality of components 21, 22 and actuators 24, wherein the actuators make possible execution of rotational movements or bending movements, for example, by use of components connected directly or indirectly to one another by actuator 24 can be rotated or bent at an angle relative to one another.

Motion device 20 can preferably be put in a passive operating state in that, although components 21, 22 are movable relative to one another, they cannot be moved actively by use of actuator 24. By use of a motion sensor system 25, which is provided on the motion device 20, the relative spatial position of components 21, 22 can be detected, in particular even when motion device 20 is placed in the passive operating state described above. By carrying out a passive movement of the motion device 20, initial motion sensor signals 26 can then be generated by use of the motion sensor system 25 and evaluated by the evaluation and control unit 10 and reflect the motion sequence carried out passively in the form of motion data BD. This motion data can then be stored in memory unit 60 or, alternatively, in the external memory unit 91. At least one of external memory unit 91 and external evaluation and control unit 92 are connected wirelessly or in a hardwired connection to the evaluation and control unit 10 by the interface 90 arranged on the evaluation and control unit 10.

Detection of motion data BD is especially advantageous when the motion device 20 is arranged on a body part 4 of a healthy person or is applied to a healthy person in the case of an exoskeleton. The healthy person then carries out a movement, whose sequence is stored in the form of motion data BD. During the movement, motion sensor system 25 detects the relative spatial positions of components 21, 22 and generates corresponding first motion sensor signals 26, which are transmitted to evaluation and control unit 10, which is connected to motion sensor system 25 and then evaluates these initial motion sensor signals 26, generating therefrom motion data BD illustrating the motion sequence, characterized in the simplest case by a starting position and an end position. By recording a plurality of relative spatial positions of components 21, 22 and generating corresponding first motion sensor signals 26, at least one of a more complex motion sequence and a motion sequence in the form of motion data BD represented in greater detail can be saved. Alternatively, it is possible to carry out the movements with the patient, wherein a therapist carries out the movements in the style of the Feldenkrais method, for example.

Motion sensor system 25 preferably also detects at least one forces and torques occurring during a movement on the motion device and generates at least one second motion sensor signal 28 which is sent to a comparator unit 120, which compares the second motion sensor signal 28 with reference data R and generates a signal 29, if a deviation is found in excess of a predefinable threshold. This signal is evaluated by the evaluation and control unit 10 connected to the comparator unit 120. In the simplest case, at least one of the occurrence of forces and torques exceeding the threshold is then displayed on at least one of a visual and acoustic display 121.

Alternatively, however, when the predefinable threshold is exceeded, possibly indicating increased arbitrary movement of the body part by the patient, other data D is used by evaluation and control unit 10 as the basis for further treatment. This data is either already stored in memory unit 60 or external memory unit 91, or the data can be determined by the evaluation and control unit 10.

However, the fact that the predefinable threshold has been exceeded can also be interpreted as a sign of a defect in the motion device and/or the need for a repair of the motion device.

Figure 4:
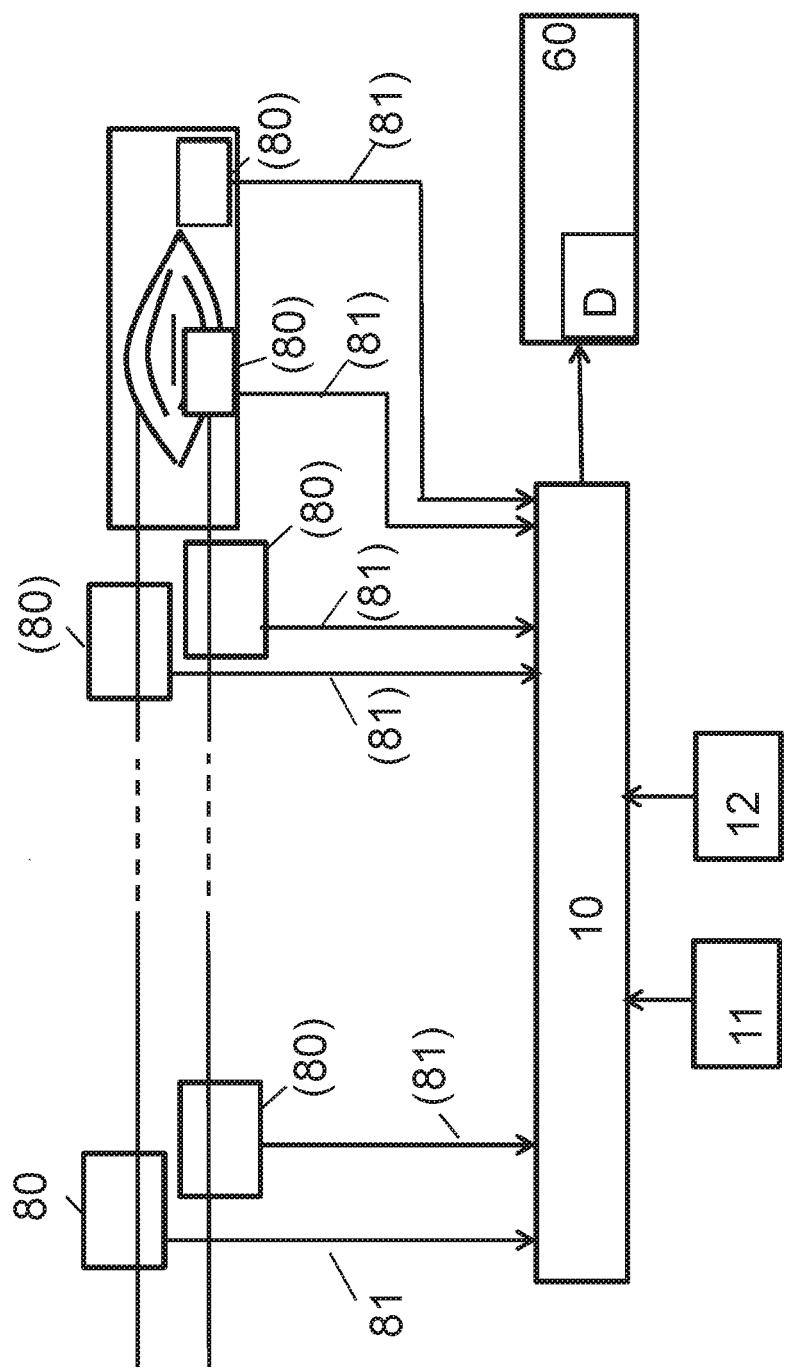
FIG. 4 shows a schematic diagram of possible locations where the preferred sensor system can be placed.

FIG. 4 shows a sensor system 80 by which a quantifiable change in state can be detected on the motor nerve conduction part 2, on the sensory nerve conduction part 3, on at least one of the skeletal muscle S and on body part 4. In this case, the sensor system 80 generates a sensor signal 81 which is evaluated by the evaluation and control unit 10 connected to the sensor system 80. FIG. 4 shows various detection sites, where the sensor system 80 can detect changes in state individually or in combination. FIG. 4 also illustrates a display module 11 connected to the evaluation and control unit 10 and an input module 12. In the simplest case the evaluation and control unit 10 is a computer, the display module 11 is a display screen and the input module 12 is one of a keyboard and a computer mouse.

Figure 5:
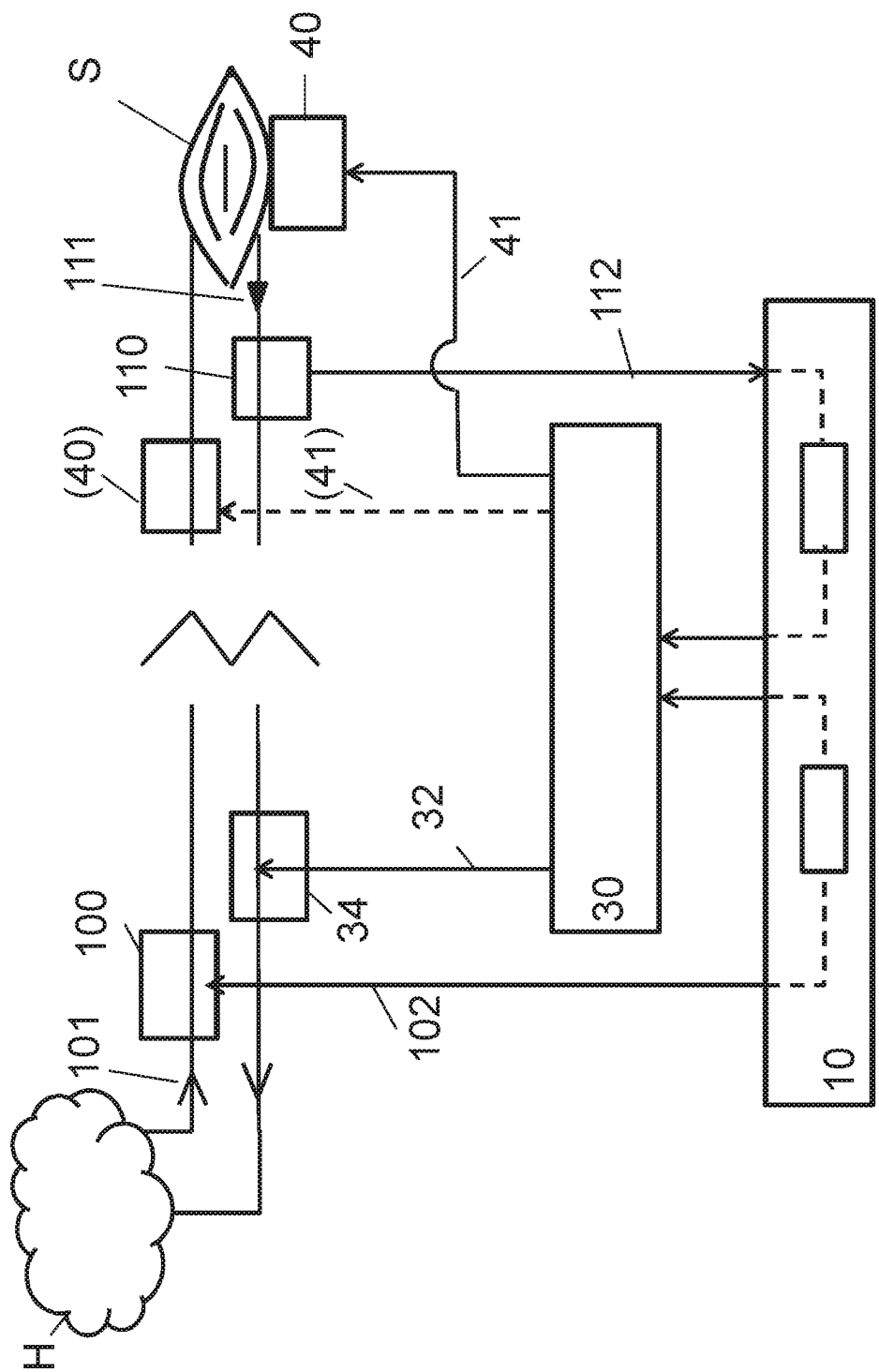
FIG. 5 shows a schematic diagram of a preferred embodiment with a first and a second sensor unit.
Figure 6:
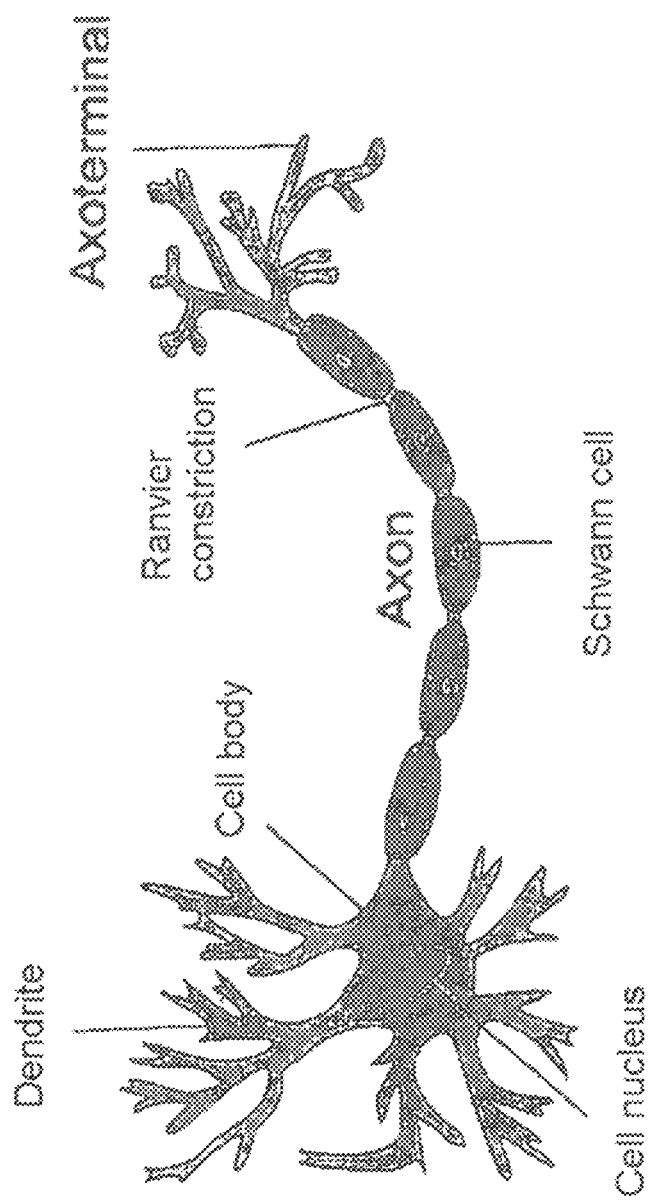
FIG. 6 shows a schematic diagram of a nerve cell with afferent cell projections (dendrites) and efferent cell projections (neurite, axon).

FIG. 5 shows a preferred embodiment with a first sensor unit 100 which detects a natural electrical nerve signal 101 intended for stimulation of the skeletal muscle S then generates at least one first sensor signal 102 which is evaluated by the evaluation and control unit 10 connected to the first sensor unit 100. The evaluation comprises at least one filtering, and at least one of one amplification and one processing of the at least one first sensor signal 102. Evaluation of the sensor signal 102 makes it possible to filter the natural nerve signal for triggering the skeletal muscle S out of at least one of the noise and out of interference signals to be able to generate a third stimulation signal 41 corresponding to this nerve signal by use of the signal generator unit which is applied to the skeletal muscle by use of the applicator 40. Due to the interaction of the first sensor unit 100, evaluation and control unit 10, signal generator unit 30 and applicator 40, the motor nerve conduction part 2 that is interrupted by the separation point is more or less bridged.

By analogy with this, a second sensor unit 110 which detects an electrical nerve signal 111 of the sensory nerve 3" at least one of connected to the skeletal muscle S and detecting activity of the skeletal muscle S is provided for bridging the sensory nerve conduction part 3 interrupted by the separation point and generates at least one second sensor signal 112 which evaluates the evaluation and control unit 10 connected to the second sensor unit 110. Here again as described above, the evaluation serves to gain a second stimulation signal 32 which corresponds to the natural signal.

Additional advantages and explanations of additional preferred embodiments of the system according to the invention:

The system according to the invention makes it possible to bridge the damaged location in the reflex arc in such a way that the reflex arc remains functionally in operation.

If necessary, stem cells which differentiate to form nerve cells in the neural environment may be introduced into the spinal cord. In this case they replace the original nerve cell. The new nerve cell can be influenced in a positive sense to "grow into" the location by administering at least one suitable messenger substances and growth factors.

Another possibility is transplanting nerve cells or "supporting cells" from other tissues into the spinal cord so that they can then support the development of new nerve cells. As in the case of stem cells, integrated new nerve cells also replace the old nerve cells. Again in this case it may be helpful to administer supporting factors.

This system is characterized in that it can maintain the natural function of a reflex arc despite damage and after damage and can thereby bring the damaged components or the new components replacing them into an environment that promotes regeneration and prevents natural degradation of biological structures due to suppressed intercellular communication. The signal generator unit 30 therefore generates a first stimulation signal 31, which it applies to the LMN at a suitable location by a first applicator 33. Furthermore, a second stimulation signal 32 is generated as feedback and delivered by a second applicator 34 to the sensory nerve cell at a suitable location.

Due to stimulation of only the sequences in the control system of the reflex arc, the muscle is not yet moved because of interrupted conduction to the muscle, although the LMN (optionally new) is active, as desired. As long as the connection between the LMN and the muscle and at least one between the muscle spindle and the sensory nerve cell has not been restored, the system will ensure that the muscle, which is normally innervated by the respective reflexive arc, is in fact being moved. This does not ultimately take place for this reason, because other existing reflex arcs, which are in a causal relationship with the movement, are preferably also taken into account (type Aγ motor neurons).

This is ensured by motion device 20. In order for this to take place in chronological and causal correlation with the sequences controlled by signal generator unit 30, both of them are controlled by an evaluation and control unit 10.

This causes a third stimulation signal 41 to be sent to the muscle via a third applicator 40 simultaneously with the first stimulation signal 31 or during the movement of the body part based on the activity of the motion device 20. Contraction of the muscle then generates, by use of the muscle spindle, a sensory signal, which may fade out due to the damaged reflex arc that can be replaced by the second stimulation signal 32. However, it also generates all the other signals that are important in the context of other control systems that are not affected. This prevents these secondary dependent control signals from degenerating due to nonuse.

Regeneration of the corrupted reflex arc can be supported in a positive sense, as described above, by administering certain factors such as at least one of messenger substances and growth factors. The system takes this into account by having an injector system 50, which can deliver these substances to the suitable site of action. This site of action is to be identified individually.

Control unit 10 carries out complex functions. The chronological sequence of stimuli and reactions to stimuli in particular are highly individual. The stimuli per se are preferably complex, not just involving short on-off pulses. Instead, additional coded information about the respective nerve cells is transmitted in the signals, that is, in the case of the signal of the muscle spindle, information about the degree of contraction of the muscle is transmitted. Then, the need for and type of an additional signal to be transmitted are calculated from the LMN from this information.

This means that the system is preferably capable of adapting to actual situations. This takes place in that it is implemented in the context of a neural network that is capable of learning or a comparable approach to data processing that is capable of learning. To this end, it deposits data in a local memory unit 60.

The type of motion device 20, with which the movement of the body part is carried out, depends on the degree and type of damage. For example, a suitable orthotic device 130 may be used if it affects an arm or if the paralysis is incomplete. However, it may also be necessary to use an entire exoskeleton in order to be able to learn to walk again in the case of paralysis-induced immobility, for example. Then the exoskeleton and orthotic device are controlled by the control under 10 and the signal unit 30. The movement patterns used in doing so are also stored in the memory unit 60 and are optionally adapted to the respective prevailing situation by use of the neural network that is capable of learning. Modifications in the form of the type and reason are also stored in the memory unit. Because of these mutual dependencies on the orthotic device or the exoskeleton 130, the evaluation and control unit 10, signal generator unit 30 and memory unit 60 are preferably arranged on the orthotic device or the exoskeleton 130 and thus form an independent unit.

It is possible to access the evaluation and control unit 10 and the memory unit 60 linked to it from external systems via an interface 90. This can take place wirelessly or via a hardwired connection. This enables the data exchange with an external evaluation and control unit 92 and its external memory unit 91. It is possible in this way to retrieve not only data for evaluation purposes from the independent unit but also to transfer data to it, for example, in order to compare and optionally modify the current movement patterns with those of other independent units. It is also possible in this way to implement not only a system capable of learning on the basis of the local prevailing situations but also a system that can take into account the experience of other systems. Multiple systems can form a mutually supportive network in this way, which is even more effective the greater the number of participants.

Motion devices 20, which comprise the orthotic device or exoskeleton, can be controlled by the evaluation and control unit 10, in that a signal from the evaluation and control unit can be sent to an actuator 24, which moves to parts 21 and 22 of the orthotic device or of the exoskeleton that are movable relative to one another, for example, by actuator motors. They also have a motion sensor system 25, with which the positions relative to one another can be detected and transmitted to the evaluation and control unit by a first motion sensor signal 26.

In addition, the motion sensor system 25 is capable of recording at least one of the forces and torques occurring with the movement and making them available as a second movement signal 28. The combination of the two movement signals can be used to describe the movement that is carried out and compare it with reference data via a comparator unit 120, for example. As a result of this comparison, the evaluation and control unit 10 can perform an evaluation of the signal 29 thereby generated and can respond to it.

Additional components with which the movement is generated and monitored by also be necessary. For example, in the case of systems which should serve the function of continued movement, it is necessary to be able to determine an absolute position of the entire system in space in addition to the positions of components 21 and 22 relative to one another. The accelerations occurring in walking are also very important and should be detected and included in the calculations.

To carry this out and then be able to implement it in an exoskeleton, for example, gyroscopic systems 140 and other suitable sensors 141, for example, acceleration sensors, are necessary to stimulate the function of the position and movement system in the human equilibrium organ and to ascertain at least one of linear and angular accelerations in all directions in space and transmit this information to the evaluation and control unit 10 for evaluation.

Treatment of paralysis is extremely individual because the anatomical and physiological prerequisites are extremely individual. It is thus necessary for the system to be able to learn the movement patterns, which are to be carried out and which it then must carry out within the context of response to the activities of the reflex arcs. Therefore, the system must have an operating mode, in which the orthotic device or the skeleton can be moved passively, but wherein it generates all the sensor signals and transmits them to the evaluation and control unit. It is possible in this way to generate a sequence of sensor signals, which represent the sequence of a fluid movement to be carried out and can be used as needed to carry out the learned movement by use of the motion device 20. The passive movement process takes place with suitable therapeutic measures, for example, according to the Feldenkrais method and/or the movements of healthy volunteers. These signal sequences are stored in the memory unit 60 as "movement patterns."

The function of the system in the context of therapy assigns nerve impulses originating from the motor cortex or from other parts of the brain responsible for the motor system and optionally having them carried out.

Like the situation with the reflex arc, it is important that the motor centers in the brain receive feedback about a movement that has been made. This feedback is necessary not only to keep the motion sequence fluid on the basis of the resulting changes in actions but it also serves to receive this important information in the movement memory of how the movement is to be triggered. If this fails to occur, as with current measures, then this could be the reason why or at least one reason why the pure restoration of nerve cells in the spinal cord, regardless of the method, has not yet been as successful as expected. On the other hand, this could also explain why there have been at least partial cures in some individual cases. In these patients, the movement information was evidently still available or could at least be reactivated.

In a manner similar to maintaining cognitive memory content such as learned knowledge, inasmuch as that which has been learned can be applied or recalled, it is necessary to receive the contents of the movement memory by carrying out the movements stored there. If this is not the case for a long period of time, the memories are deleted, just as is the case with what you learn in school, after it has not been accessed for a long time. The system should preferably have a mechanism for transmitting feedback about a movement initiated to the brain centers involved even in a case of compromised stimulus conduction in paralysis.

Therefore, the first sensor unit 100, which can detect signals 101 sent from the brain to the spinal cord via the medulla oblongata, then sends them further as detector signals 102 to evaluation and control unit 10, which analyzes the signals on the basis of data D stored in memory unit 60, among other things, and assigns the data to a movement pattern, which is also integrated there and has been "learned.", in response to a clear-cut stimulus from the brain, it can trigger a motion sequence stored in the brain for the orthotic device or the exoskeleton 130. At the same time, a third stimulation signal 41 is transmitted to the skeletal muscle (S) via signal generator unit 30 and applicator 40. This synchronizes stimulation of the activity of the motor part of the reflex arc with the movement to be carried out.

Feedback to the brain area takes place in the form of a second sensor unit 110, which can detect a signal 111 of an intact sensory nerve SP, the sensor itself MS or an activity of the muscle S and generates a second sensor signal 112, which prompts the stimulation unit 30 by way of the evaluation and control unit 10 to trigger the second stimulation signal 32. This mechanism also synchronizes the movement to be carried out, in this case with the activity of the sensory part of the reflex arc.

This is not a trivial process because, like leads for brain currents (EEG), the signals from the brain obtained by use of the sensor unit 100 are a mixture of hundreds and thousands of signals of individual first neurons (UMN) and their sensory analogs because the respective nerve fibers usually cannot be addressed directly. The situation is similar for the signals of the sensor unit 110 derived for feedback because, as already explained above, there is not just one source of sensory information for each muscle. Therefore, a self-learning capability of the system and thus at least a portion of the implementation of the evaluation and control unit in the form of a neural network—or something comparable—is required.

It may be helpful to first have a healthy volunteer carry out the movements with the system in the passive mode. The signals 26 to 29 thereby generated by the motion sensor 25 can be related to the signals 101. This helps not only to be able to give feedback to the motor centers of the brain but also to determine the type and chronological sequence of the first stimulation signal 31 and the second stimulation signal 32 which are necessary for stimulation of the reflex arc.

The neural network can define a basic setting in this way with which the system can operate and which is then adapted subsequently to the respective patient in that the self-learning system recognizes what is needed for adaptation and performs that act. By use of the data exchange 90 with other systems and control units 91 and their memory systems 92, the individual particulars for other patients can then be verified to ascertain whether they could be helpful with the current patient—and then to make appropriate corrections.

It may also be helpful to substantially reduce the number of interfering signals received by the sensor system 100. This can be achieved by stopping superfluous motor activities. This is difficult for a patient who is conscious, but it can be achieved easily if the patient is put in a trancelike state, which is possible through meditation or hypnosis. This state can be detected by using leads to record the brainwaves (EEG) because their frequency and amplitude form a measure of brain activity. A patient can still respond while in a trance state, but brainwaves picked up as theta waves in this condition indicate that most cerebral activity has been stopped—including movements. Administering the treatment under hypnosis/meditation thus seems to facilitate analysis of the required signals, at least in a "learning phase" of the system.

Hypnosis/meditation is also advantageous for another reason. Learning movements is an unconscious process and is therefore not subject to arbitrary influence. To be sure, movements can be carried out intentionally but this is limited to a higher level of the movement process. Which activities take place at the level of the nerve stimuli, which are to be triggered and when, in which sequence and with which intensity are not factors that are controlled consciously, as is the case for saving the movement pattern resulting therefrom in the movement memory.

However, there has been good experience in getting a response out of the movement center and optionally modifying it with patients who have lost their mobility due to other causes. Thus, a combination of hypnosis and the Feldenkrais method in patients in whom the motor center in the cerebral cortex had to be removed completely or partially due to tumors yielded amazing results that could not have been achieved by traditional rehabilitation measures. The problems are similar in these patients. To be sure, the reflex arcs that are so important are still functioning in the spinal cord, but new nerve cells had to take over the task of the nerve cells that had been removed in areas of the brain that previously had nothing to do with movement. This is obviously possible and the process seems to be more promising with the use of hypnosis alone than without the use of hypnosis.

Therefore, part of this system is a detector 70 capable of detecting electrical brain signals, with which it is possible to evaluate the current degree of consciousness and transmit this information by use of a detector signal 71 to the evaluation and control unit 10. This can then perform its movements and activities resulting therefrom as a function of the state of consciousness. It is also conceivable in particular in the learning phase of the system to allow movements only if the patient is hypnotized.

Various items of information are necessary to correctly reflect the complicated interaction of mutual dependencies and to trigger corresponding activities. In addition, the system must be able to detect and assess the entire range from complete execution of a motion sequence (ideally) on the basis of a brain signal without any other natural activities (condition immediately after the onset of paralysis) up to a strict monitoring function (at the end of treatment). It is therefore necessary for the system to be self-learning.

Interfaces as between the system and the biological system in the form of applicators 33, 34 and 40, with which it can deliver pulses to this system. Therefore, signals that fail to occur from the reflex arc are simulated, as is also feedback to the brain.

Interfaces as between the system and the biological system in the form of sensor units 100 and 110, with which pulses can be obtained from the biological system to control the activities. To obtain a complete overview of the current situation, what is missing is sensors within the reflex arc, which notify the system of how little friction there is with the flow of information taking place within this lower level.

This information is important because it enables the system to make decisions about which partial aspects are to be simulated in the reflex arc (motor, sensory or motor and sensory simulation), to which extent it must be active as dominant, supporting or monitoring and to which extent the two control systems are to be synchronized. Thus, for example, after functional restoration of the reflex arc, there could be a need to continue to send feedback to the brain in order not to forget the old or newly learned movement patterns—which is important in the training phase in particular.

There is preferably at least one sensor 80, which detects the activity of the nerve cell to be integrated or the regenerating nerve cell and generates a sensor signal 81, which is made available to the evaluation and control unit 10. The number and location of these sensors 80 depend on the respective case individually. If only the motor part is corrupted, it must sit on the LMN at a location that allows an evaluation of whether the cell is viable and can send nerve pulses over an axon. If the sensory part is corrupted, this also applies similarly to the spinal ganglion.

Additional locations of such sensors include the muscles and the body part itself for discovering muscle activities.

Signals generated in this way can also be used for controlling the injector system 50.

The system according to the invention is not primarily intended to be used as a technical assistant to improve the long-term quality of life. The system has primarily therapeutic importance with the goal of short-term to medium-term avoidance of the system if no further improvement can be achieved by using the system as part of a therapy. In the ideal case, this is the case after achieving complete restoration of function.

If this is impossible, the individual information (movement patterns) collected by the system as part of the therapeutic measures, can be used to establish simpler embodiments that are optimized individually and are used as technical medical assistants. In this way the exoskeleton or orthotic device can be produced with a complexity that could not previously be achieved and will allow the patient a new quality of life.

Use of the invention serves the purpose of the most extensive possible restoration of movement abilities lost due to paralysis but also serves the purpose of treatment of incomplete paralysis ("paresis," e.g. peroneal paresis="dorsiflexion paralysis"). It should make technical aids that have become necessary, such as orthotic devices/ exoskeletons, superfluous by leading to independent movement, starting with forced movement thanks to the invention, by training and increasing withdrawal of the self-learning system (assisted movement). In practical terms, this takes place in three phases:

1. Passive Learning Phase

With the exoskeleton/orthotic device in place, the movements that the patient is supposed to practice are carried out on the patient in a passive operating mode through suitable measures, such as the Feldenkrais method with/without hypnosis. The motion sensor system 25 on the motion device 20 thereby detects the position of components 21 and 22 with respect to one another as well as other changes that occur during the movement, for example, linear acceleration and angular acceleration (cf. FIG. 3), and relays this information as the first movement signals 26 to control unit 10, which evaluates this motion data BD and stores it chronologically as movement patterns BM in data memory unit 60. These patterns represent the joint positions that are possible individually relative to one another and occur in a fluid movement.

Already in this early phase, it is advisable to transfer this data to the external database 91 via the interface 90 and have it analyzed by the external evaluation unit 92. In this way, the data can be compared with movement patterns obtained from healthy people with natural movements, without having a therapist compel the movement manually. In addition, comparison with data records from other patients is also possible. By comparing all these data records with the data currently transmitted about the patient, it is possible to ascertain correction values, which can be submitted to control unit 10 via interface 90 again to be taken into account.

The motion data ascertained in this phase also serves as reference data R, with which comparator unit 120 will later compare the second movement signal 28 in an active operating mode and will optionally generate the signal 29.

In this phase, control unit 10 also detects signals 81 of sensors 80 (cf. FIG. 4). It is possible in this way to ascertain which components of the control system, and at least one of motor and sensory information can be generated naturally at all with movements and what the quality is. It is possible in this way to decide which of the stimulation signals 31, 32 must be generated by the signal generator unit 30 in the later active phase and in which intensity (cf. FIG. 1).

Finally, in this phase, the signal 101 optionally coming from the UMN is detected by the first sensor unit 100 and transmitted as the first sensor signal 102 to the control unit 10. The situation is similar with the feedback signal 111, which is intended for feedback to the sensory nerve cell in the brain and, present in this way, is detected by use of the second sensor unit 110 and transmitted in the form of the second sensor signal 112 to the control unit 10. In this way, the interaction of the two intermeshing control systems can be detected, and, if necessary, the signal generator unit 30 can generate signals 32 and 41, which are necessary for maintaining the higher-level control system and preserving the movement memory (cf. FIG. 5).

2. Active Learning Phase

In an active operating mode, the movement patterns determined in the passive learning phase are used, to be carried out either individually or in any context. The sequences to be learned can be repeated as often as desired. They are selected by means of either input devices 11 and output devices 12 (cf. FIG. 4) or triggered by evaluation of signals 101 (cf. FIG. 5), if possible.

In this phase the invention is used in two ways:

(1) For active, assisted or forced movement where the control unit 10 controls the movement unit 20 and specifically the actuator 24 that moves components 21 and 22 about the joint 23 relative to one another (FIG. 3). In doing so, the data about the motion sensor system 25 is detected and sent back as feedback to the control unit 10 via the first motion sensor signal 26. At the same time the comparative unit 120 is prompted by use of the second motion sensor signal 28 to compare the data with the stored reference values R and to generate a corrective signal 29, if necessary, and relay it to the control unit 10 for evaluation.

Changes occurring here in the movement pattern carried out are saved in the memory unit 60 to optionally be forwarded via the interface 90 at the same time or later for evaluation to the external control unit 92, which also stores these patterns in the external memory unit and sends consequences of the evaluation back to the control unit 10.

(2) For active, assisted or forced signal processing of the control systems, wherein, as in the passive learning phase, the motor sensor signals and sensory sensor signals 81 are picked up, if they occur at all, upstream and downstream from the damaged site by means of sensor system 80. Simultaneously with carrying out the movement, now the missing or inadequately manifested stimuli are stimulated by stimulation signals 31, 32 and 41 and fed into the control system with the LMN via applicators 33, 34 and 40 (FIG. 2). By evaluation of the differences in the type and quality of the incoming signals 81 in different runs, the necessity and quantity of stimulation signals 31, 32 and 44 can be influenced. The goal is to be able to do without them in the long run.

The active learning phase is a cyclic process carrying out saved movement patterns, the associated movement, detection of the resulting sensor signals, their evaluation and the resulting adaptation of the movement patterns and signals as well as saving them in external data banks. This is concluded when no more adaptations are necessary and the system has all the necessary data. Furthermore it serves analyze the complex patterns, which are detected as the first sensor signal 102 from the first sensor 100 and to filter out the signals which correspond to the triggering of the desired muscle.

Since this active learning phase comprises a large number of processes, the system learns independently to adjust to the current patient, so that an optimal individual therapy is possible. At the same time, by comparison with similar cases in the external memory unit 91, there may be indications about which additional measures/changes might be appropriate. The change in individual movement patterns as part of an additional passive learning phase during training is also possible because to do so the movement must simply be "impressed" from the outside (e.g., by use of the Feldenkrais method) (correction and fine tuning).

All the sequences can be carried out with or without the use of additional measures such as meditation, hypnosis, stem cell therapy, nerve cell transplantation or stimulation of nerve growth. The changes in responses to these measures as well as the findings based on biofeedback all enter into the calculations.

3. Training Phase

The training phase differs from the active learning phase only in that the system no longer performs changes in the movement/signal patterns. In the training phase the sensor signals 81 are also detected and evaluated but in this phase the evaluation serves only to ascertain to what extent the system can withdraw from the forced operation and subsequently assisted operation. It is terminated when either no stimulation signals 31, 32 and/or 41 are necessary any longer (restitution to original condition), so the patient can move again completely on his own, or the required stimulus quality/intensity can no longer be reduced over a long period of time (residual damage).

It is also possible to return from the training phase back to the active or even passive learning phase if necessary.

REFERENCE LIST 1 nerve conduit
2 motor nerve conduction part
2' motor nerve conduction part, separated from the skeletal muscle
2" motor nerve conduction part, connected to the skeletal muscle
3 sensory nerve conduction part
3' sensory nerve conduction part, separated from the skeletal muscle
3" sensory nerve conduction part, connected to the skeletal muscle
4 body part
5 separation point, functional interruption in nerve conduction
10 evaluation and control unit
11 display module
12 input module
20 motion device
21, 22 components
23 joint
24 actuator
25 motion sensor system
26 first motion sensor signal
28 second motion sensor signal
29 correction signal
30 signal generator unit
31 first stimulation signal
32 second stimulation signal
33 first applicator
34 second applicator
40 third applicator
41 third stimulation signal
50 injector system
60 memory unit
70 detector unit
71 detector signal
80 sensor system
81 sensor signal
90 interface
91 external memory unit
92 external evaluation and control unit
100 first sensor unit
101 natural nerve signal intended for stimulation of the skeletal muscle
102 first sensor signal
110 second sensor unit
111 nerve signal of the sensory nerve connected to the skeletal muscle
112 second sensor signal
120 comparator unit
121 optical or acoustic display
130 power supply unit
140 gyroscope
141 acceleration sensors
S skeletal muscle
D data
MS muscle spindle
R reference data

The invention claimed is:

1. A system for regeneration of at least one severed nerve conduit, configured for use in a living human or animal body, the at least one nerve conduit comprising at least one motor nerve conduction part and at least one sensory nerve conduction part,
the system comprising:
a motion device including means, configured for moving a body part of the human or animal body, the body part containing at least one skeletal muscle that is otherwise innervatable with the at least one severed nerve conduit, the motion device including an orthotic device or an exoskeleton;
a signal generator which generates a first electrical stimulation signal and a second electrical stimulation signal;
an evaluation and control including means, which controls the motion device and the signal generator to be coordinated with one another so that the signal generator is configured to apply the first electrical stimulation signal to the at least one motor nerve conduction part which is separated from the skeletal muscle by use of a first applicator, and the motion device is configured to move the body part in a chronological coincidence therewith, and during or after the movement of the body part, the signal generator applies the second stimulation signal via the first applicator or a second applicator to the sensory nerve conduction part which is separated from the skeletal muscle; and wherein
with the motor nerve conduction part is a portion of the nerve conduit for conducting signals emanating from at least one of the brain and the spinal cord for triggering the at least one skeletal muscle and the sensory nerve conduction part is a nerve conduit for conducting signals emanating from at least one of the at least one skeletal muscle and a biological sensor in functional contact with the at least one skeletal muscle to at least one of the brain and the spinal cord.

2. The system according to claim 1, wherein:
the signal generator is configured to generate a third electrical stimulation signal for application to the skeletal muscle by a third applicator; and
the evaluation and control controls the signal generator so that the third stimulation signal is applicable to the skeletal muscle simultaneously with the first stimulation signal or while the motion device is moving the body part.

3. The system according to claim 1, comprising:
an injector system which is configured to be controlled by the evaluation and control and to apply at least one active ingredient in an area of the at least one severed nerve conduit.

4. The system according to claim 1, comprising:
at least one memory which is configured to store data, and wherein
based on the stored data, the evaluation and control is configured to control the motion device and the signal generator.

5. The system according to claim 1, wherein:
at least one of the first applicator and the second applicator includes an electrode array.

6. The system according to claim 2, wherein:
the third applicator includes an electrode array.

7. The system according to claim 1, wherein:
the evaluation and control, and the signal generator and the memory are contained on the orthotic device or the exoskeleton.

8. The system according to claim 1, wherein:
the motion device includes at least two components connected together by a joint and includes at least one actuator by which the components are movable relative to one another; and
the at least one actuator is controllable by the evaluation and control.

9. The system according to claim 8, comprising:
a motion sensor located on the motion device which detects at least a relative spatial position of components of the motion sensor and generates at least one motion sensor signal which is evaluated by the evaluation and control.

10. The system according to claim 9, wherein:
when the system is in an operating state, the motion device is movable without the support of at least one of the at least one actuator and the evaluation and control; and
the evaluation and control generates motion data in the operating state based on the first motion sensor signal generated by the motion sensor system that is stored in the memory.

11. The system according to claim 9, wherein:
the motion sensor system detects at least one of forces and torques occurring on the motion device during movement and generates at least one second motion sensor signal; and
comprises a comparator which compares the second motion sensor signal with reference data and, if a deviation between the at least one second motion sensor signal and the reference data exceeding a preselectable threshold is found, the comparator generates a signal; and
the comparator is coupled to the evaluation and control which evaluates the signal generated by the comparator.

12. The system according to claim 4, comprising:
a detector configured to detect electrical brain signals and generate a detector signal; and
the detector is connected to the evaluation and control which evaluates the detector signal and controls the motion device and the signal generator in accordance with data stored in the at least one memory.

13. The system according to claim 1, wherein:
the evaluation and control includes an interface which is connectable wirelessly or by a hardwiring to at least one of an external memory and at least one external evaluation and control.

14. The system according to claim 2, comprising:
a first sensor which detects a natural electrical nerve signal for stimulating of the skeletal muscle and generates at least one first sensor signal;
the first sensor is connected to the evaluation and control unit; and
the evaluation and control evaluates the first sensor signal and controls the signal generator based on the first sensor signal which generates the third stimulation signal.

15. The system according to claim 1, comprising:
a second sensor which detects at least one of an electrical nerve signal of the sensory nerve conduction part, configured for connection to the skeletal muscle, and an activity of the skeletal muscle, and which generates at least one second sensor signal;
the second sensor is connected to the evaluation and control which evaluates the second sensor signal and controls the signal generator based on the evaluated second sensor signal to generate the second stimulation signal.

16. The system according to claim 1, comprising:
a sensor system for detecting a quantifiable change in state and generating a sensor signal of at least one of a group of the motor nerve conduction part, the sensory nerve conduction part, the skeletal muscle and the body part; and
the sensor system is connected to the evaluation and control which evaluates the generated sensor signal.

17. A method for regenerating at least one severed nerve conduit in a living human or animal body, the at least one nerve conduit comprising at least one motor nerve conduction part and at least one sensory nerve conduction part,
the human or animal body containing a body part having at least one skeletal muscle that would otherwise be innervatable with the severed nerve conduit, comprising the steps of:
generating a first electrical stimulation signal;
applying the first electrical stimulation signal to the motor nerve conduction part separated from the skeletal muscle of the at least one severed nerve conduit;
moving the body part in chronological coincidence with application of the first electrical stimulation signal to the motor nerve conduction part which is separated from the skeletal muscle;
generating a second electrical stimulation signal; and
applying the second electrical stimulation signal during or after the movement of the body part on the sensory nerve conduction part which is separated from the skeletal muscle; and wherein
with the motor nerve conduction part is a portion of the nerve conduit for conducting signals emanating from at least one of a brain and a spinal cord for triggering the at least one skeletal muscle and the sensory nerve conduction part being a nerve conduit for conducting signals emanating from at least one of the at least one skeletal muscle and a biological sensor in functional contact with the at least one skeletal muscle to at least one of the brain and the spinal cord.

18. The method according to claim 17, wherein:
a third electrical stimulation signal is generated; and
the third electrical stimulation signal is applied to the skeletal muscle simultaneously with the first stimulation signal or while carrying out the movement of the body part.

19. The method according to claim 17, wherein:
before, during or after application of at least one of the first and second electrical stimulation signals, an active ingredient is applied in the area of the severed nerve conduit.

* * * * *